US009289142B2

United States Patent
Kong et al.

(10) Patent No.: US 9,289,142 B2
(45) Date of Patent: Mar. 22, 2016

(54) IMPLANTABLE ELECTRODE LEAD SYSTEM WITH A THREE DIMENSIONAL ARRANGEMENT AND METHOD OF MAKING THE SAME

(71) Applicant: NeuroNexus Technologies, Inc., Clarenc, NY (US)

(72) Inventors: Kc Kong, Ann Arbor, MI (US); Jamille Farraye Hetke, Brooklyn, MI (US); James A. Wiler, Brighton, MI (US); David S. Pellinen, Ann Arbor, MI (US); Mayurachat Ning Gulari, Ann Arbor, OH (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 369 days.

(21) Appl. No.: 13/750,420

(22) Filed: Jan. 25, 2013

(65) Prior Publication Data

US 2013/0137955 A1  May 30, 2013

Related U.S. Application Data

(63) Continuation-in-part of application No. 12/410,253, filed on Mar. 24, 2009, now abandoned.

(60) Provisional application No. 61/039,085, filed on Mar. 24, 2008.

(51) Int. Cl.
*A61B 5/04* (2006.01)
*A61N 1/05* (2006.01)
(Continued)

(52) U.S. Cl.
CPC .............. *A61B 5/04* (2013.01); *A61B 5/04001* (2013.01); *A61B 5/685* (2013.01); *A61N 1/05* (2013.01);
(Continued)

(58) Field of Classification Search
CPC ......... A61N 5/04; A61N 1/05; A61N 1/0534; A61B 5/04001; A61B 5/04022; A61B 5/0492; A61M 25/0147; H05K 1/00
USPC .......................................... 607/116; 600/373
See application file for complete search history.

(56) References Cited

U.S. PATENT DOCUMENTS

| 3,921,916 A | 11/1975 | Bassous |
| 4,461,304 A | 7/1984 | Kuperstein |

(Continued)

FOREIGN PATENT DOCUMENTS

| WO | PCT/CA00/00942 | 2/2001 |
| WO | PCT/EP00/10775 | 5/2002 |

(Continued)

OTHER PUBLICATIONS

Seymour et al., "Neural probe design for reduced tissue encapsulation in DNS" 28 (2007) 3594-3607, Apr. 5, 2007.

(Continued)

*Primary Examiner* — Niketa Patel
*Assistant Examiner* — Lindsey G Hankins
(74) *Attorney, Agent, or Firm* — Michael F. Scalise

(57) ABSTRACT

One embodiment of the invention includes an implantable electrode lead system that includes a series of shims stacked upon each other, a series of first components, and a series of second components connected to the series of first components through a series of connectors. One of the first components extends from one of the shims, and another of the first components extends from another one of the shims. The shims position the first components in a three dimensional arrangement.

26 Claims, 12 Drawing Sheets

(51) Int. Cl.
*A61B 5/00* (2006.01)
*A61B 5/0492* (2006.01)
*A61M 25/01* (2006.01)
*H05K 1/00* (2006.01)
*H05K 1/14* (2006.01)

(52) U.S. Cl.
CPC ............ *A61N 1/0529* (2013.01); *A61N 1/0534* (2013.01); *A61B 5/0492* (2013.01); *A61B 2562/125* (2013.01); *A61B 2562/166* (2013.01); *A61B 2562/227* (2013.01); *A61M 25/0147* (2013.01); *H05K 1/00* (2013.01); *H05K 1/147* (2013.01)

(56) References Cited

U.S. PATENT DOCUMENTS

| | | | |
|---|---|---|---|
| 4,904,237 | A | 2/1990 | Janese |
| 5,207,709 | A | 5/1993 | Picha |
| 5,308,442 | A | 5/1994 | Taub et al. |
| 5,385,635 | A | 1/1995 | O'Neill |
| 5,585,827 | A | 12/1996 | Murakami |
| 5,588,597 | A | 12/1996 | Reinecke et al. |
| 5,938,694 | A | 8/1999 | Jaraczewski et al. |
| 6,205,361 | B1 | 3/2001 | Kuzma et al. |
| 6,228,111 | B1 | 5/2001 | Tormala et al. |
| 6,324,435 | B1 * | 11/2001 | Shchervinsky et al. ....... 607/152 |
| 6,374,143 | B1 | 4/2002 | Berrang et al. |
| 6,473,653 | B1 | 10/2002 | Schallhorn et al. |
| 6,834,200 | B2 | 12/2004 | Moxon et al. |
| 6,878,643 | B2 | 4/2005 | Krulevitch et al. |
| 7,010,356 | B2 | 3/2006 | Jog et al. |
| 7,146,221 | B2 | 12/2006 | Krulevitch et al. |
| 2002/0198446 | A1 | 12/2002 | Hill et al. |
| 2003/0100823 | A1 | 5/2003 | Kipke et al. |
| 2004/0097805 | A1 | 5/2004 | Verard et al. |
| 2004/0106169 | A1 | 6/2004 | Evans |
| 2004/0199235 | A1 | 10/2004 | Younis |
| 2005/0004627 | A1 | 1/2005 | Gibson et al. |
| 2005/0021117 | A1 | 1/2005 | He et al. |
| 2005/0137647 | A1 | 6/2005 | Wallace et al. |
| 2006/0149319 | A1 | 7/2006 | Kuo et al. |
| 2006/0247749 | A1 | 11/2006 | Colvin |
| 2006/0258951 | A1 | 11/2006 | Bleich et al. |
| 2006/0276866 | A1 | 12/2006 | McCreery |
| 2006/0282014 | A1 | 12/2006 | Kipke et al. |
| 2007/0073130 | A1 | 3/2007 | Finch et al. |
| 2007/0123765 | A1 | 5/2007 | Hetke et al. |
| 2007/0135885 | A1 | 6/2007 | Risi |
| 2008/0039916 | A1 | 2/2008 | Colliou et al. |
| 2008/0208283 | A1 * | 8/2008 | Vetter et al. ...................... 607/45 |
| 2009/0048638 | A1 * | 2/2009 | Rey et al. ......................... 607/37 |
| 2009/0105776 | A1 * | 4/2009 | Aldridge et al. ................... 607/2 |
| 2009/0118806 | A1 | 5/2009 | Vetter et al. |
| 2009/0132042 | A1 | 5/2009 | Hetke et al. |
| 2009/0187196 | A1 | 7/2009 | Vetter et al. |
| 2009/0248118 | A1 | 10/2009 | Bradley et al. |
| 2010/0030298 | A1 | 2/2010 | Martens et al. |

FOREIGN PATENT DOCUMENTS

| | | |
|---|---|---|
| WO | PCT/US02/16942 | 12/2002 |
| WO | PCT/US2004/035030 | 5/2005 |
| WO | 2011/010257 | 1/2011 |

OTHER PUBLICATIONS

Seymour et al, "The insulation performance of reactive parylene films in implantable electronic devcices", Biomaterials 30 (2009) 6158-6167, Aug. 22, 2009.

Kaplan et al., "A Novel Fabrication Method of Capillary Tubes on Quartz for Chemical Analysis Applications" IEEE Proceedings, Micro Electro Mechanical Systems, Jan. 25-28, 1994.

Lin et al., "Silicon Processed Mirconeedles" The 7th International Conference on Solid State Sensors and Actuators; Jun. 7-10, 1993.

* cited by examiner

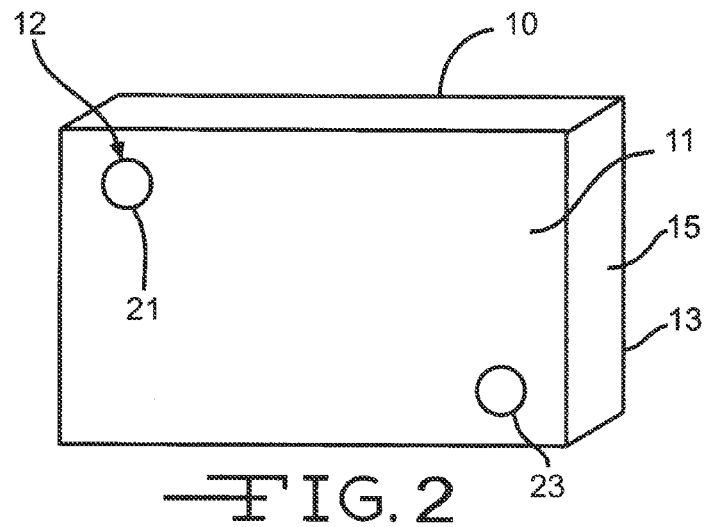
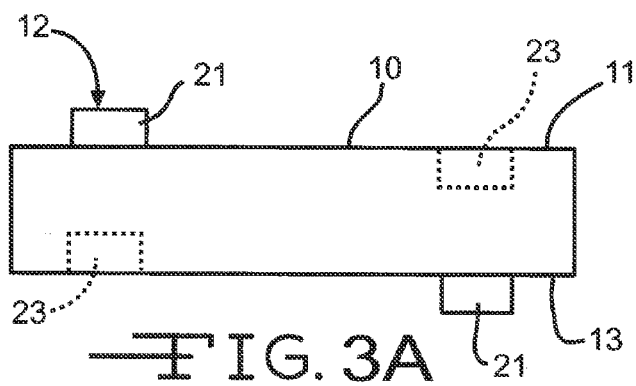
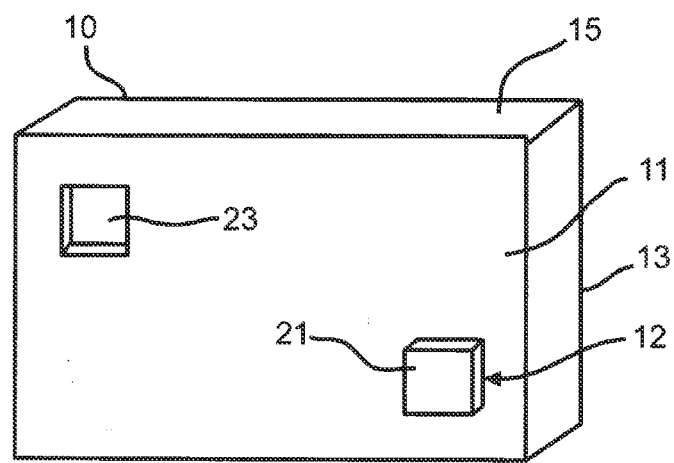

SIDE VIEW

IMPLANTABLE ELECTRODE LEAD SYSTEM WITH A THREE DIMENSIONAL ARRANGEMENT AND METHOD OF MAKING THE SAME

CROSS-REFERENCE TO RELATED APPLICATIONS

This application is a continuation-in-part of U.S. patent application Ser. No. 12/410,253, filed on Mar. 24, 2009, now abandoned, which claims the benefit of U.S. Provisional Application Ser. No. 61/039,085, filed on 24 Mar. 2008 and entitled "Three-Dimensional System of Electrode Leads and Method of Making the Same", which are incorporated in its entirety by this reference.

TECHNICAL FIELD

This invention relates generally to the electrode lead field, and more specifically to an improved three-dimensional system of electrode leads and the method of making this improved system.

BACKGROUND

Conventional brain interfaces involve electrical stimulation and/or recording from neural ensembles through an electrode lead system implanted in a targeted region of the brain. While conventional electrical stimulation therapy is generally safe and effective for reducing cardinal symptoms of approved diseases, it often has significant behavioral and cognitive side effects and limits on performance. Additionally, the therapeutic effect is highly a function of electrode site position with respect to the targeted volume of tissue and, more specifically, a function, of the influence of the delivered charge on the particular neuronal structures proximate to the charge. Neural recording applications, such as cortical neuroprostheses, often involve recording from large-scale neural ensembles in sophisticated brain structures, which have 3-dimensional anatomical shapes. With conventional electrode lead systems there are limitations on complete and precise sampling and stimulation of the desirable neural structure since electrode sites are generally positioned in a 2-dimensional fashion. Additionally, conventional three-dimensional electrode lead systems are limited by their complexity and low fabrication yield. Thus, there is a need for an improved electrode lead systems to provide fine electrode positioning, selectivity, precise stimulation patterning, and precise electrode lead location. This invention provides such an improved and useful system of electrode leads and a method of making this improved system.

BRIEF DESCRIPTION OF THE FIGURES

FIG. 2 is a perspective view of the shim and a first variation of the alignment features.

FIGS. 3A and 3B are top views and front perspective views, respectively, of the shim and a second variation of the alignment features.

DESCRIPTION OF THE PREFERRED EMBODIMENTS

The following description of preferred embodiments of the invention is not intended to limit the invention to these embodiments, but rather to enable any person skilled in the art to make and use this invention.

Figure 1:
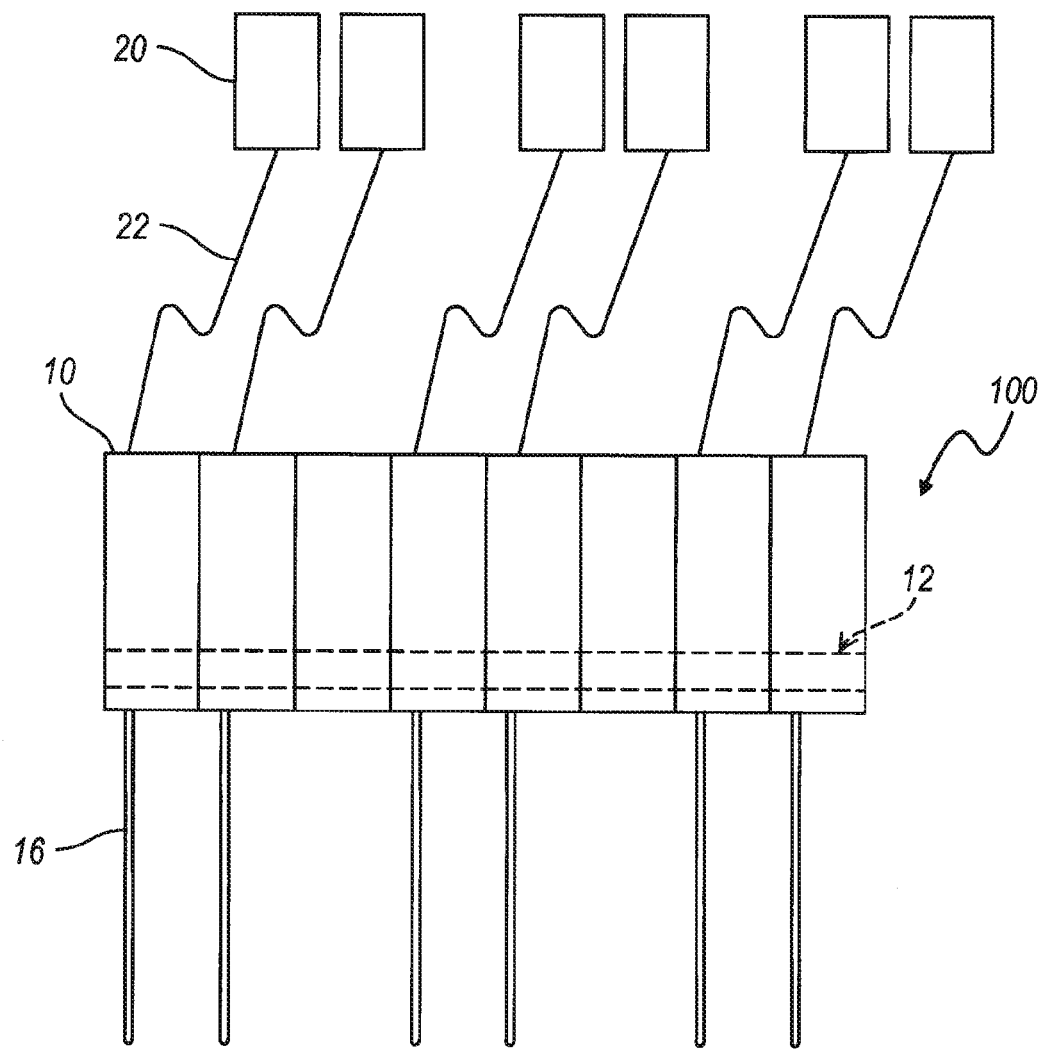
FIG. 1 is a side view of the electrode lead system of the preferred embodiment including a series of shims and a series of components.

As shown in FIG. 1, the electrode lead system 100 of the preferred embodiments includes a series of shims 10, each having an alignment feature 12, a series of components 16 in a three dimensional arrangement, a series of second components 20, and a series of connectors 22 that connect the series of components 16 to the series of second components 20. The series of shims 10 of the preferred embodiment functions to position the series of components 16 in a three dimensional arrangement and to provide a controlled and configurable spacing between the components. As shown in FIG. 2, each shim 10 of the preferred embodiments includes an alignment feature 12 that functions to provide an alignment guide such that multiple shims 10 may be assembled together. The shim 10 may further include a component receptacle 14 that functions to receive a component 16 (shown in FIG. 6 and described below). The system 100 of the preferred embodiment is preferably designed for an implantable electrode lead system to interface with brain tissue, and more specifically, for an implantable electrode lead system that can interface with brain tissue in a three-dimensional manner. The system 100 of the preferred embodiments, however, may be alternatively used in any suitable environment (such as the spinal cord, peripheral nerve, muscle, or any other suitable anatomical location) and for recording, stimulation, chemical delivery, or any other suitable reason.

1. The Shim

As shown in FIGS. 2, 3A, 3B 4A, 4B, 5A and 5B, the shim 10 comprises an upper shim surface 11 spaced apart from a lower shim surface 13 by a sidewall 15 having a sidewall thickness measured between the upper and lower surfaces 11, 13. The shim 10 comprises at least a first shim recess 17 and a second shim recess 19, both recesses 17, 19 extending from one of the upper and lower shim surfaces 11, 13 and through a portion of the thickness of the sidewall 15. The first and second shim recesses 17, 19 are spaced apart from each other and both meet a receptacle 14 in the shim 10 that is open to one of the upper and lower surfaces 11, 13, but not the other of them so that the receptacle 14 has a depth that extends only part way through the thickness of the shim sidewall 15. In one embodiment, the upper and lower surfaces 11, 13 are planar.

Figure 6:
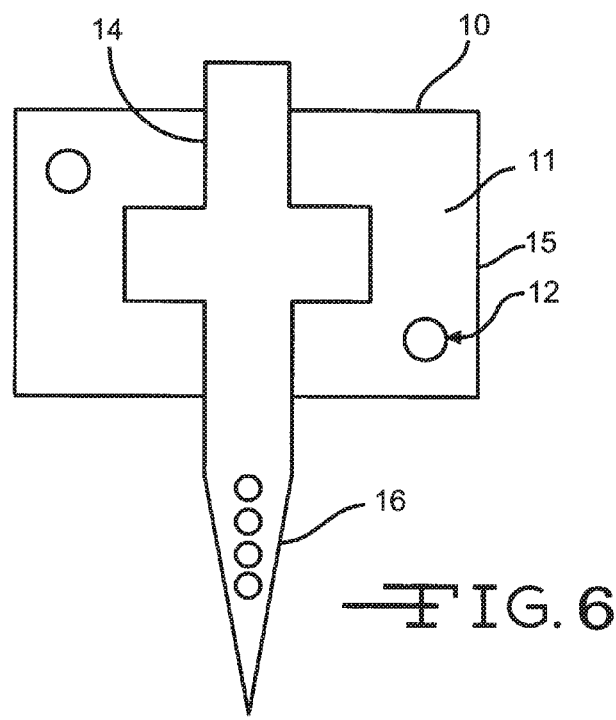
FIG. 6 is a representation of the shim of FIGS. 4a and 4B, shown with a first variation of a component.

Further, the one of the upper and lower shim surfaces 11, 13 having the receptacle 14 has an alignment feature 12 comprising at least one of a protrusion 21 and a hole 23 that is not in communication with the receptacle 14. The hole 23 provided in one of the upper and lower shim surfaces 11, 13 is located between the receptacle 14 and the shim sidewall 15 and extends either part way into or completely through the thickness of the shim 10. The other of the upper and lower shim surfaces 11, 13 opposite the receptacle 14 further comprises at least one of a protrusion 21 and a hole 23. FIG. 3A illustrates the protrusion 21 and hole 23 comprising male and female mating elements. FIG. 6 shows the receptacle 14 as a cross-shaped cavity.

The series of shims 10 of the preferred embodiment functions to position the series of components 16 in a three dimensional arrangement. The shims 10 provide a controlled and configurable spacing between the components 16. Each shim 10 in the series of shims may optionally remain empty, may position a single component 16, or may position more than one component 16. Therefore, the electrode lead system 100 may include one shim 10 for every component 16, such that the ratio of shims 10 to components 16 in the electrode lead system 100 is 1:1; the electrode lead system 100 may include one shim 10 for every two or more components 16, such that the ratio of shims 10 to components 16 in the electrode lead system 100 is less than 1:1; or there may be shims 10 without a component 16, as shown in FIG. 1, such that the ratio of shims 10 to components 16 in the electrode lead system 100 is greater than 1:1. The electrode lead system 100 preferably includes any suitable combination of shims 10 that position zero, one, or more than one components 16.

The shim 10 of the preferred embodiment is preferably generally planar with a specified thickness. The thickness determines the controlled and configurable spacing of the components 16 of the electrode lead system 100. The specified thickness is preferably determined by the thickness of each individual component 16 and the desired component-to-component spacing. The shims 10 are preferably rectangular, but may alternatively have any suitable geometry. The shims are preferably a silicon substrate, but may alternatively be made from any other suitable material such as metal or polymer.

As shown in FIGS. 2 and 3, the shim 10 of the preferred embodiment includes an alignment feature 12. The alignment feature 12 functions to provide an alignment guide such that multiple shims 10 may be assembled together using the alignment features 12 of each shim 10. The alignment features 12 are preferably fabricated with the shim 10 using microfabrication techniques, but may be made in any other suitable fashion with any suitable material. The alignment feature is preferably one of several variations. In a first variation, as shown in FIG. 2, the alignment feature 12 is a hole defined by the shim 10. The hole is preferably located toward the outer edge of the shim 10, but may alternatively be located in any suitable location on the shim 10. In this variation, the shim 10 may define any suitable number of alignment features 12. In a second variation, as shown in FIGS. 3A and 3B, the alignment feature 12 includes male and female mating elements. As shown in FIG. 3A, the protruding alignment feature 12 located in the bottom right hand corner of the shim 10 has a corresponding recessed element defined by the shim 10. The protruding feature, or male element, will mate with a recessed, or female element, on a second shim 10 in a manner similar to LEGO brand building blocks. The alignment features 12 in this variation may be located in any suitable location. In a third variation, the alignment feature 12 is the shape of the shim 10. As an example, the shim 10 may have two opposing surfaces: a convex surface and concave surface. The two opposing surfaces preferably mate together in a manner similar to PRINGLES brand potato chips. Although the alignment feature 12 is preferably one of these variations, the alignment feature 12 of the preferred embodiment may be any suitable alignment feature in any suitable location on or around the shim 10 such that multiple shims 10 may be assembled together using the alignment features 12 of each shim 10.

Figure 4A:
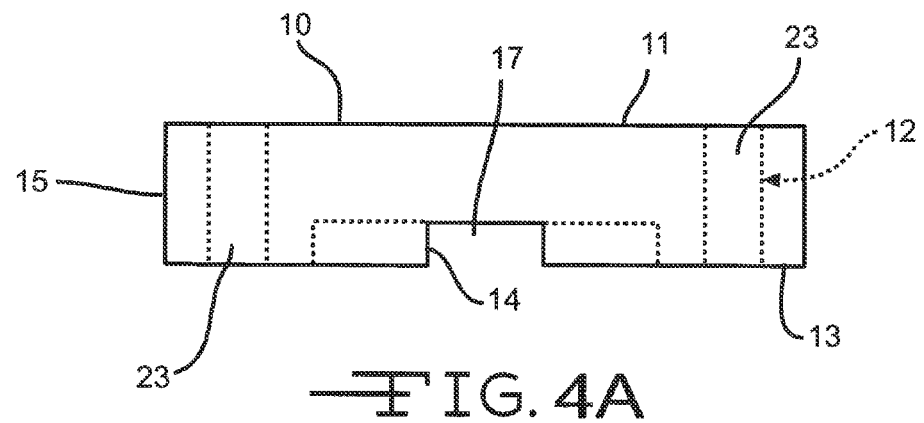
FIGS. 4A and 4B are top views and front views, respectively, of the shim, the first variation of the alignment features, and a first variation of the component receptacle.
Figure 4B:
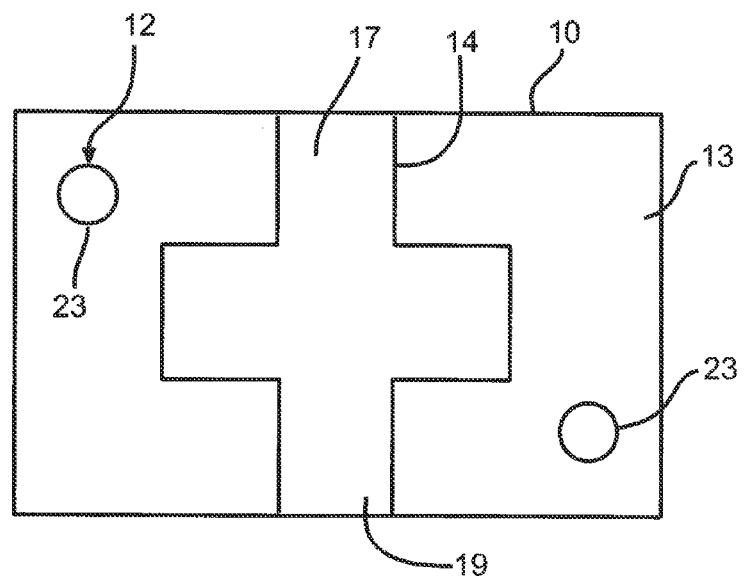
Figure 5A:
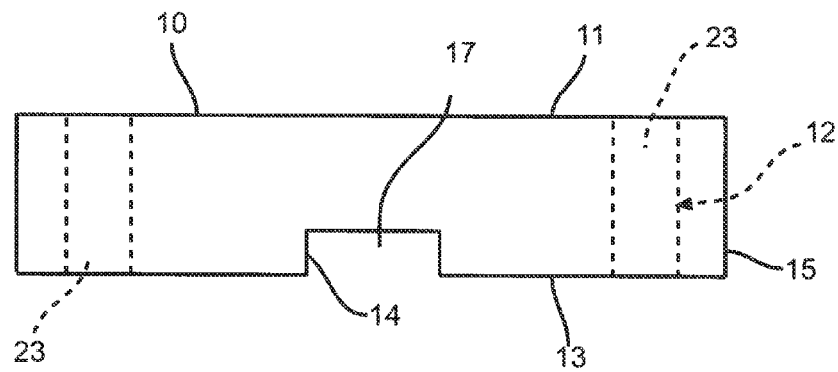
FIGS. 5A and 5B are top views and front views, respectively, of the shim, the first variation of the alignment features, and a second variation of the component receptacle.
Figure 5B:
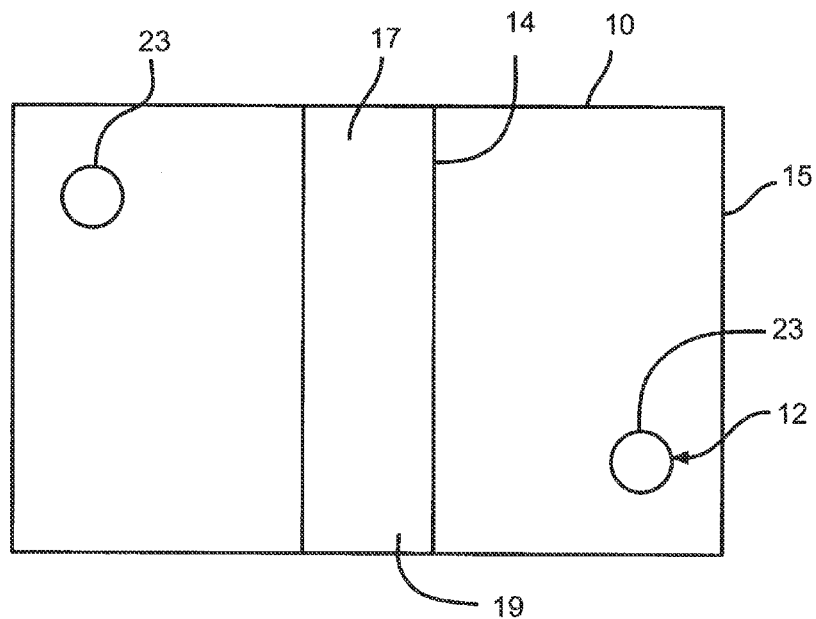

As shown in FIGS. 4A, 4B, 5A and 5B, the shim 10 of the preferred embodiment may further include a component receptacle 14 that functions to receive a component 16. The component receptacle 14 is preferably adapted to receive one component 16, but may alternatively remain empty or receive more than one component 16. The component receptacle is preferably a cavity (or "negative") of the component to be received by the component receptacle 14, but may alternatively be any other suitable shape, such as a generic shape adapted to fit multiple different components. The depth of the component receptacle 14 is preferably a few microns deeper than the depth of the component 16 to be received by the component receptacle 14, but may alternatively be any other suitable depth. The component receptacle 14 is preferably fabricated with the shim 10 using microfabrication techniques, but may be made in any other suitable fashion with any suitable material. The component receptacle 14 is preferably one of several variations. In a first variation, as shown in FIGS. 4A and 4B, the component receptacle is preferably a cross like shape adapted to receive a planar electrode array (shown in FIG. 6). This variation preferably provides anchoring in multiple dimensions. In a second variation, as shown in FIGS. 5A and 5B, the component receptacle is preferably a cylindrical recess adapted to receive a fluidic component. This variation preferably provides anchoring in at least one dimension. Although the component receptacle 14 is preferably one of these variations, the component receptacle may have any suitable geometry and any suitable depth or attachment mechanism to receive a component 16.

Figure 11:
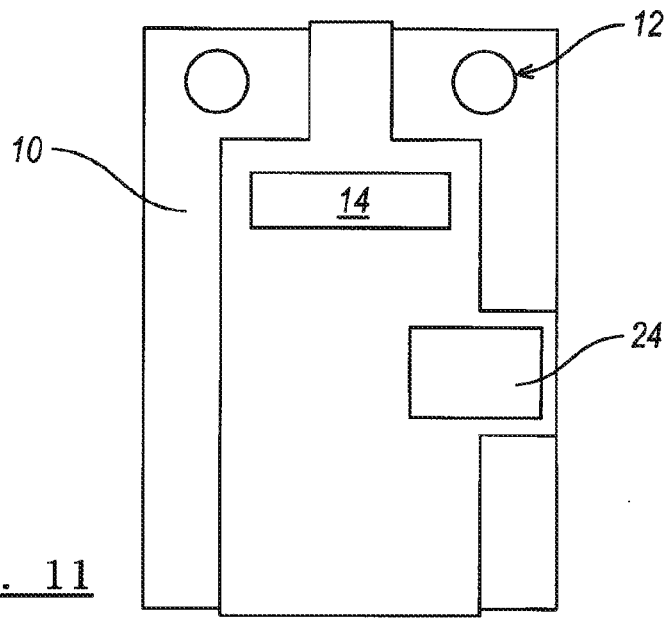
FIG. 11 is a representation of the top view of a shim.

As shown in FIG. 11, the shim 10 of the preferred embodiment may further include an injection port 24. The injection port 24 functions to facilitate the backfilling of epoxy into the cavity or negative of the shim 10 during the assembly of the electrode lead system 100, which is described in more detail in Section 5: Method of Assembly.

The shim 10 may also include one or more integrated circuits (e.g., Application Specific Integrated Circuit, or ASICs) to interface with amplifiers, filters, signal processors, multiplexors, power, memory units, fluid flow controllers, or any suitable electrical component. The shim 10 may also include a fluid reservoir for filling fluidic components.

The cavity of the shim may also include connection pads to allow for direct integration of the components 16 to the shim and on-shim ASICs. The top surface of the shim may also include shim interconnection pads that electrically connect the shim to another shim and/or the connector 22. The shim interconnection pads may have equal or fewer pads than the number of active electrode sites depending on the circuitry, such as a multiplexor, in the ASIC.

2. Method of Making the Shim

Figure 10A:
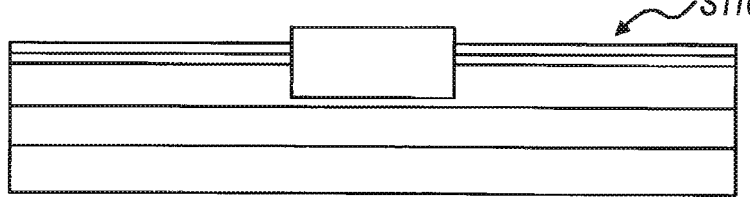
FIGS. 10A to 10C are schematics of a method of making a shim pictured in a series of side views.
Figure 10B:
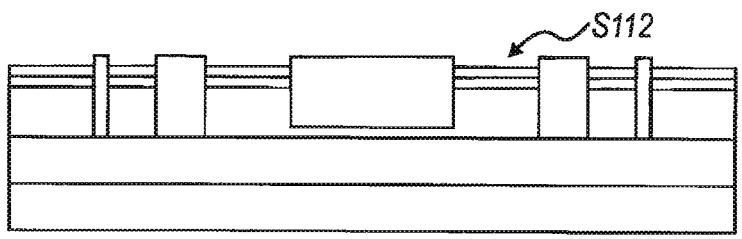
Figure 10C:

The shims 10 of the preferred embodiment, including the alignment feature 12 and the component receptacle 14, are preferably micro-machined using standard microfabrication techniques, but may alternatively be fabricated in any other suitable fashion. The method of the preferred embodiments, as shown in FIGS. 10A to 10C, includes providing a wafer, removing a portion of the wafer S110 (FIG. 10A), creating an alignment feature S112 (FIG. 10B), and releasing the shims from the wafer (FIG. 10C). The method is preferably designed for the manufacture of a series of shims. The method, however, may be alternatively used in any suitable environment and for any suitable reason.

The step of providing a wafer functions to provide a foundation from which to build the series of shims 10. The wafer is preferably a standard wafer conventionally used in semiconductor device fabrication and more preferably a SOI wafer (silicon-insulator-silicon substrate), but may alternatively be any suitable wafer, such as a wafer with a machinable silicon substrate and a release mechanism. The wafer is preferably made from silicon, but may alternatively be made from gallium arsenide, indium phosphide, or any other suitable material. The wafer is preferably manufactured with an oxide layer buried a specified distance below the top surface. The depth or thickness of the buried oxide layer preferably determines the thickness of the shim 10. The wafer preferably has the same thickness as the specified thickness of the shim 10, such as 50 µm, 100 µm, or any other suitable thickness.

Step S110, which includes removing a portion of the wafer, functions to define the geometry and the depth of the component receptacle 14. Additionally, this step may also define the injection port 24. This step is preferably performed through a deep reactive ion etching (DRIE), but may alternatively be performed through any other suitable removal process, such as other dry etching methods, wet etching, chemical-mechanical planarization, or any combination thereof. Removing material is preferably performed after providing a patterned thermal oxidation and masking such that the unmasked material is removed. This step preferably includes a photolithographic mask. Alternatively, the shim 10 may be built up, using any suitable deposition technique, around the geometry of the component receptacle 14 to define the component receptacle in that manner. The component receptacle may alternatively be created by any suitable combination of deposition, removal, and or patterning. The dimensions of the component receptacle 14 are preferably as close to the dimensions of the component 16 as possible to maintain the lateral alignment of the component 16 within the shim 10, while there is some tolerance between the component 16 and the component receptacle 14 to allow the component 16 to be easily disposed into the component receptacle 14. The tolerance is preferably less than 100 µm and more preferably less than 10 µm. The depth of the component receptacle is preferably less than 100 µm deep and more preferably about 85 µm deep such that it will completely enclose the component 16 and connector 22 junction, which includes the thickness of the component 16 (about 15 µm), the thickness of the connector 22 (about 15 µm), and the height required for interconnection with an ultrasonic ball bond, flip chip technique or another suitable interconnection method (typically 50 µm or less). The tolerances and thickness of the components and components receptacles may alternatively be any other suitable thickness or depth respectively.

Step S112, which includes creating an alignment feature 12, functions to build an alignment feature 12 on the shim 10. This step may further function to define the shape and size of the shim 10. The alignment features 12 may be created by removing material or by adding material. The removal of material is preferably performed through a deep reactive ion etching (DRIE), but may alternatively be performed through any other suitable removal, process, such as other dry etching methods, wet etching, chemical-mechanical planarization, or any combination thereof. Removing material is preferably performed after providing a patterned thermal oxidation and after masking such that the unmasked material is removed. The addition of material is preferably performed through any suitable deposition process that grows, coats, or transfers a material onto the wafer in any other suitable method. These deposition processes may include physical vapor deposition (PVD), chemical vapor deposition (CVD), electrochemical deposition (ECD), molecular beam epitaxy (MBE), atomic layer deposition (ALD), or any other suitable process. The alignment features may alternatively be created by any suitable combination of deposition, removal, and or patterning.

The final step, which includes releasing the shims 10 from the wafer, completes the process and releases the manufactured shims 10. This step is preferably completed by dissolving the built-in sacrificial oxide layer, releasing the shims 10 from the wafer, but may be accomplished in any suitable manner.

3. The Component

The series of components 16 of the preferred embodiments function to interface with the tissue, or any other suitable substance, within which they have been implanted. The series of components 16 may include any combination of similar or different electrical and/or fluidic components. The component 16 is preferably one of several variations.

In a first variation, as shown in FIG. 6, the component 16 is a neural interface electrode array, similar to the neural interface electrode array described in US Publication No. 2008/0208283 published on 28 Aug. 2008 and entitled "Neural Interface System", which is incorporated in its entirety by this reference. The electrode array preferably has a plurality of electrode sites and is generally two-dimensional or planar. The electrode sites are preferably tuned for recording, stimulation, chemical sensing, any other suitable function, or any combination thereof. The electrode array may further include fluidic channels providing the capability to deliver therapeutic drugs, drugs to inhibit biologic response to the implant, or any other suitable fluid. The neural interface electrode array is preferably made from a substrate such that there is high density of electrode sites at a first end of the array (the distal end) and bonding regions at a second end of the array (the proximal end). The substrate is preferably silicon, but may alternatively be a thin-film polymer substrate. The polymer substrate is preferably parylene or some combination of parylene and inorganic dielectrics, but may alternatively be made out of any suitable material. The electrode sites are preferably patterned directly onto the substrate. The electrode array is preferably comprised of conductive interconnects disposed between layers of dielectrics that insulate the interconnects on top and bottom sides. At least some interconnects preferably terminate with electrode sites on the distal end and/or with bond pads for electrical connection to external instrumentation and/or hybrid chips on the proximal end. The electrode sites are preferably metal such as iridium, platinum, gold, but may alternatively be any other suitable material. The electrode sites may alternatively undergo further processing such as electroplating and/or site selective coating to tune impedance, increase stimulation level, and/or to release drugs. The conductive leads or traces are preferably metal or polysilicon, but may alternatively be any other suitable material. Polyimide, parylene, inorganic dielectrics, or a composite stack of silicon dioxide and silicon nitride is preferably used for the dielectrics, but any other suitable materials may alternatively be used.

In a second variation, the component 16 is a mapping electrode array, which functions to perform clinical deep brain electrophysiological mapping for use in neurosurgical applications. More specifically, the mapping electrode array is preferably adapted to perform simultaneous multichannel neural recording from precisely known locations along the deep microelectrode track. The mapping electrode may further have extended functionality such as multichannel recording and/or stimulation or fluid delivery. The mapping electrode system is preferably a planar electrode array disposed on an insulated metal wire. The metal wire is preferably made from a metal such as tungsten, stainless steel, platinum-iridium, or any other suitable metal. The electrode array preferably includes multiple recording sites.

In a third variation, the component is a fluidic component. The fluidic component in this variation is preferably a flexible micro fluidic tube, but may alternatively be any suitable tube, channel, planar electrode array (with or without electrode sites), or any other suitable component to transmit fluid. Although the component 16 is preferably one of these variations, the component 16 may be any suitable element or combination of elements to perform the desired functions.

4. The Second Component the Connector, and the Third Component

The series of second components 20 of the preferred embodiments function to operate with the first component 16. The second component 20 may include multiple different electrical subsystems or a series of the same subsystems. The electrode lead system 100 preferably includes a second component for every component 16, such that the ratio of second components to components 16 is 1:1. By including one second component 20 for every component 16, the electrode lead system 1001 is a modular system with a decreased chance of failure of the entire electrode lead system 100 due to a failure of a single component 16. Alternatively, the electrode lead system 100 may include one second component for every two or more components 16, such that the ratio of second components to components 16 is less than 1:1 or may include two or more second components for every component 16, such that the ratio of second components to components 16 is greater than 1:1.

Figure 14A:
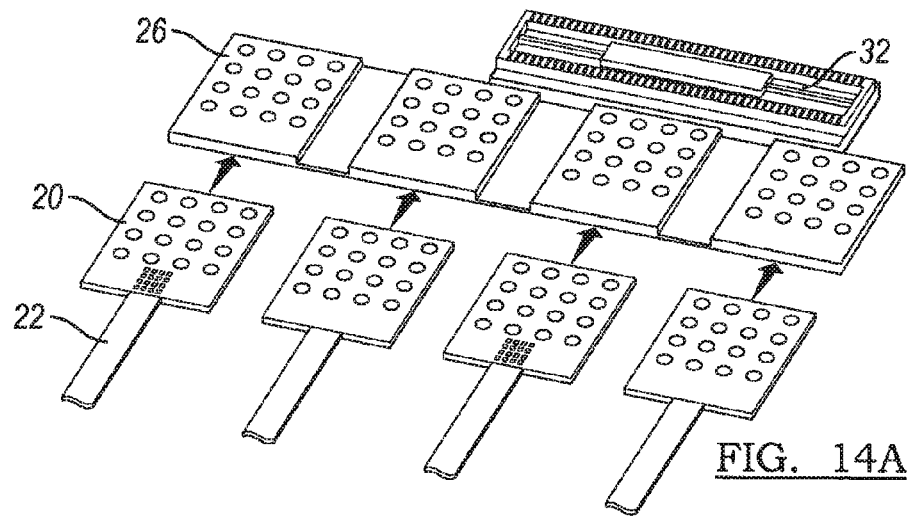
FIGS. 14A to 14D are representations of a series of connectors, a series of second components, and a series of third components of the electrode lead system of the preferred embodiment.
Figure 14B:
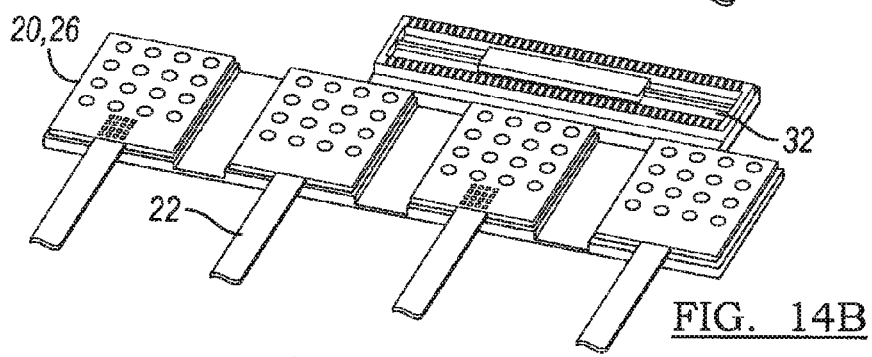
Figure 15A:
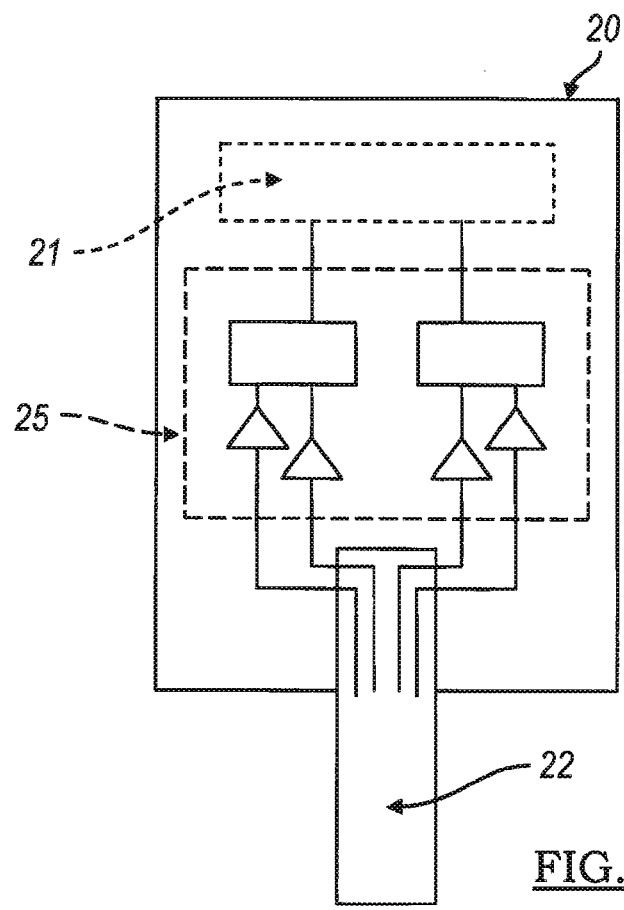
FIGS. 15A and 15B are top views and bottom views, respectively, of the second component of the electrode lead system of the preferred embodiment.

The second component is a suitable electronic and/or fluidic subsystem to operate with the component 16. Preferably, as shown for example in FIG. 14A, the second component 20 is a printed circuit board (PCB). As shown in FIG. 15A, the second component 20 preferably includes on-board integrated circuits and/or on chip circuitry 25 for multiplexing, signal conditioning, stimulus generation and/or other suitable functions. The PCBs of the second components 20 are preferably made from flexible PCB that is approximately 100 μm thick, but may alternatively have any suitable thickness. The PCBs of the second components 20 may alternatively be made of thin rigid PCBs. Alternatively, the second component 20 may be an Application Specific Integrated Circuit (ASIC), a multiplexer chip, a buffer amplifier, an electronics interface, an implantable pulse generator, an implantable rechargeable battery, integrated electronics for either real-time signal processing of the input (recorded) or output (stimulation) signals, integrated electronics for control of the fluidic components, any other suitable electrical subsystem, or any combination thereof. Although the second component is preferably one of these several subsystems, the second component may be any suitable element or combination of elements to operate any suitable first component(s) 16.

Figure 15B:
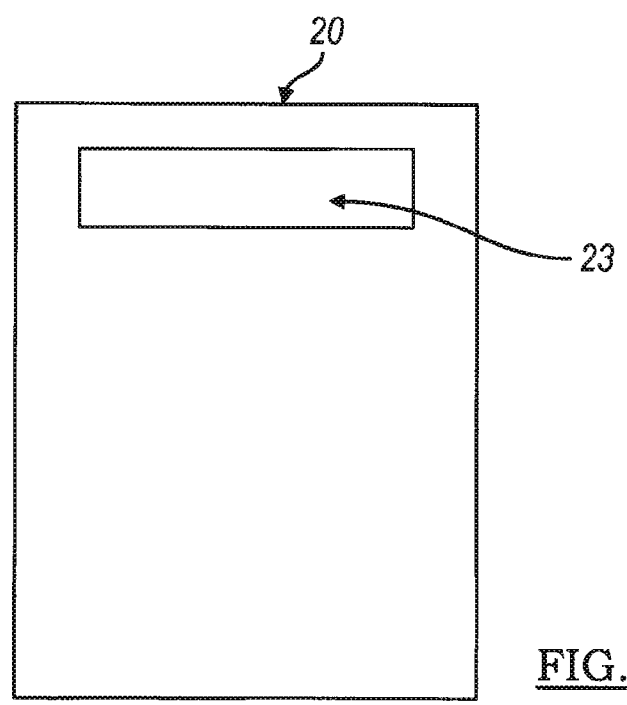
Figure 16:
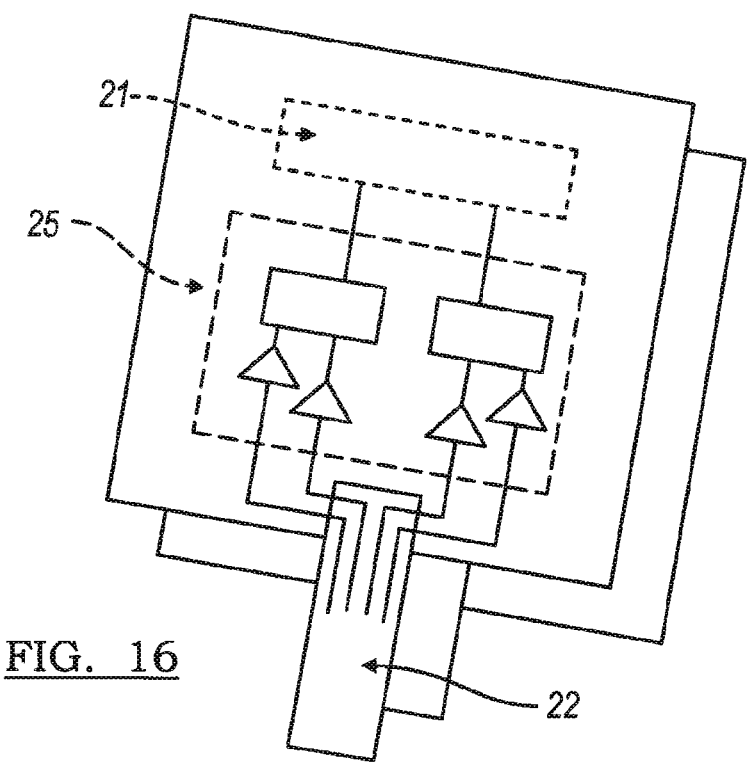
FIG. 16 is a representation of the interconnection feature of a series of second components of the electrode lead system of the preferred embodiment.

The second component 20 may include one or more mutually coupling interconnection features to enable multiple second components 20 to be coupled to one another and/or to the third component 26. As shown in FIGS. 15A and 15B, the mutually coupling interconnection feature is preferably a mating pair of low profile, zero-insertion-force (ZIF) connectors of opposite genders 21 and 23 (such as Hirose Electric, Japan), but may alternatively be any number of any suitable kind of connector. Each second component 20 preferably has a female connector 21 located on a top face (FIG. 15A) and a male connector 23 located on a bottom face (FIG. 15B), in such a way that as shown in FIG. 16, multiple second components 20 are coupled in a stack by mating female and male connectors 21 and 23 of adjacent second components 20. Alternatively, the female connector 21 may be located on a bottom face of the second component 20 and the male connector 23 may be located on a top face of the second component 20 to allow adjacent second components 20 to couple in a similar fashion. Alternatively, the mutually coupling feature may be a set of interconnection pads that are coupled together by soldering, flip chip techniques, or any suitable coupling method.

The total number of active channels required for the self-coupling interconnection feature is calculated by multiplying of the number of electrode sites from each first component 16 by the number of second components to be coupled together. Alternatively, the total number of active channels required for the mutually coupling interconnection feature can be reduced by utilizing the onboard multiplexing circuitries such that the ratio of active interconnection channels to the total number of the electrode sites from the electrode lead assembly 100 is 1:2 or greater.

The connector 22 of the preferred embodiments functions to couple the first components 16 to the second components 20. The connector may be encased in silicone or any other suitable material. In some situations, the component 16 may have multiple connectors. Preferably, multiple connectors are physically attached along their entire length, using a suitable adhesive such as medical grade adhesive or any other suitable connection mechanism. The connector is preferably connected to the components 16 through ball bonds, flip chip technique, or any other suitable connection mechanism and/or method. Alternatively, the connector may be seamlessly manufactured with the first and/or second component such that it is an integrated connector. The connector may further include fluidic channels adapted to deliver therapeutic drugs, drugs to inhibit biologic response to the implant, or any other suitable fluid.

The connector 22 is preferably one of several variations. In a first variation, the connector is a silicon ribbon cable. The ribbon cable in this variation is preferably an integrated ribbon cable with the silicon substrate of the component 16, but may alternatively be connected in any suitable fashion. In a second variation, the ribbon cable is a polymer ribbon cable. The ribbon cable in this variation is preferably connected to the component 16 via ball bonds or any suitable mechanical connection, but may alternatively be connected in any suitable fashion. Although the connector is preferably one of this variations, the connector may alternatively be any suitable element to couple the first components 16 to the second components, such as wires, conductive interconnects, etc.

Figure 12:
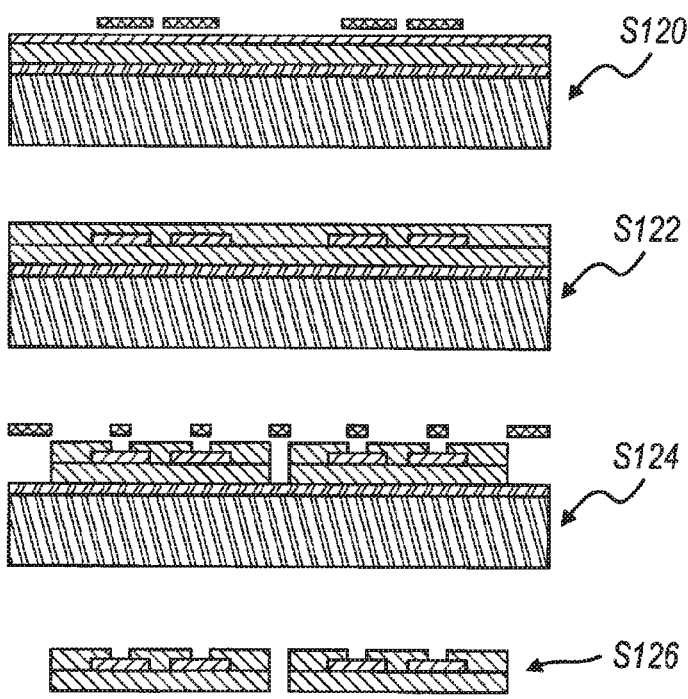
FIG. 12 is a schematic of a method of making a connector pictured in a series of side views.

The connector 22 is preferably fabricated using a microfabrication process. In a first variation, as shown in FIG. 12, the connector 22 is preferably fabricated using a polyimide microfabrication process. The process preferably includes two masks. Fabrication preferably starts on a silicon wafer onto which a sacrificial oxide is thermally grown to provide a mechanism for device release. The lower layer of polyimide, (e.g., PI-2611, HD Microsystems) is spun on, partially cured, and plasma etched through a first mask to promote adhesion of the metal leads 5120. In this variation, gold and an adhesion layer of titanium are next deposited using evaporation 5120, with preferable layer thicknesses of 250 nm gold and 30 nm titanium, although gold and titanium may be deposited to any suitable thicknesses. The gold and titanium layers are then patterned and etched to define the leads, and the upper polyimide is spun on and fully cured S122. An etch, preferably an oxygen and tetrafluoromethane etch, removes the field and open apertures through a second mask that will form the bond pads S124. Finally, after the wafers are cleaned, the devices are released from the wafer by dissolving the sacrificial oxide 5126. In this variation, connector 22 thickness is preferably about 15 mm, but can be modified by changing the thickness of either the top or bottom polyimide layer. The pad layout of the connector 22 at the distal end is preferably designed to interface with the component 16 bond pads to permit ultrasonic ball bonding between the component 16 and the connector 22. The thickness or height of the bond pad region of the component 16/connector 22 junction is preferably less than 1,000 µm, and more preferably less than 100 µm.

Figure 14C:
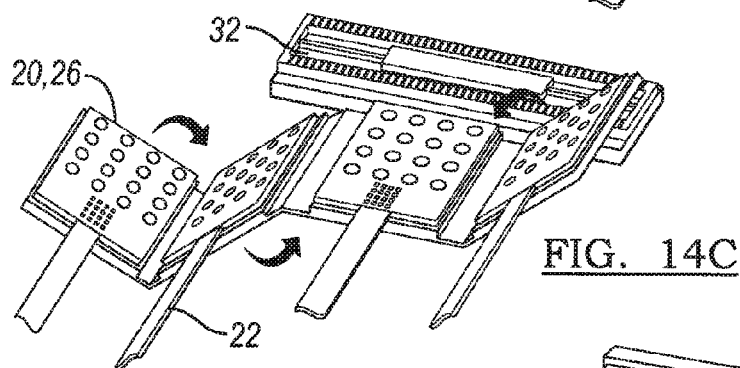
Figure 14D:
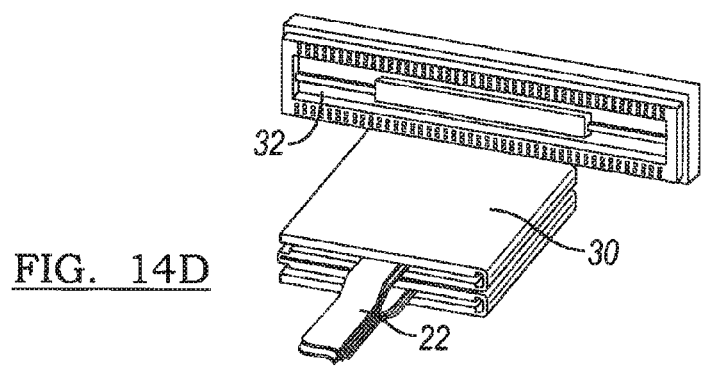
Figure 17:
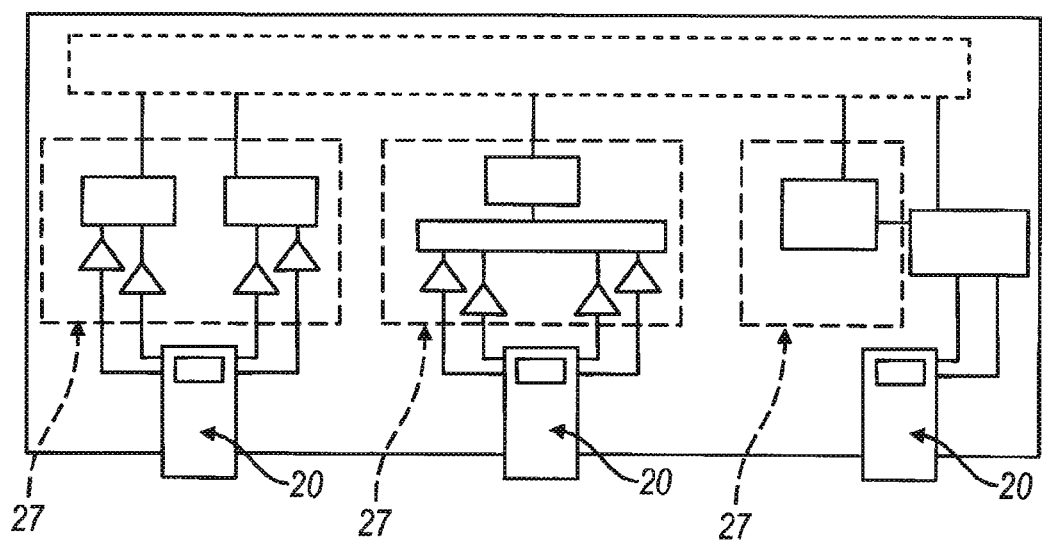
FIG. 17 is a representation of a series of second components and the third component of the electrode lead system of the preferred embodiment.

The third component 26 is a suitable system that couples to one or more second components 20 as shown in FIGS. 14 to 14C and 17 and includes input/output connectors to provide a unified interface to access the electrode sites of the electrode lead system 100. The third component 26 is preferably made of rigid PCB and as shown in FIG. 17, preferably includes on-board integrated circuits and/or on-chip circuitry 27 for multiplexing, signal conditioning, stimulus generation, battery powering, wireless communication, and/or any other suitable functions. The third component 26 is preferably coupled to the second component 20 with one or more permanent and/or non-permanent connection methods identical to the connection methods for coupling the connector 22 to the second component 20, and described in more detail in Section 5: Method of Assembly. However, the third component 26 may alternatively be coupled to the second component 20 with any other suitable method. Alternatively, the third component 26 can be made of flexible PCB. In this variation, multiple second components 20 can be attached to the third component 26, and as shown in FIG. 14C, the footprint of the third component 26 can be reduced by folding the flexible circuits. The folding of the flexible circuits is described in more detail in Section 5: Method of Assembly.

Figure 8A:
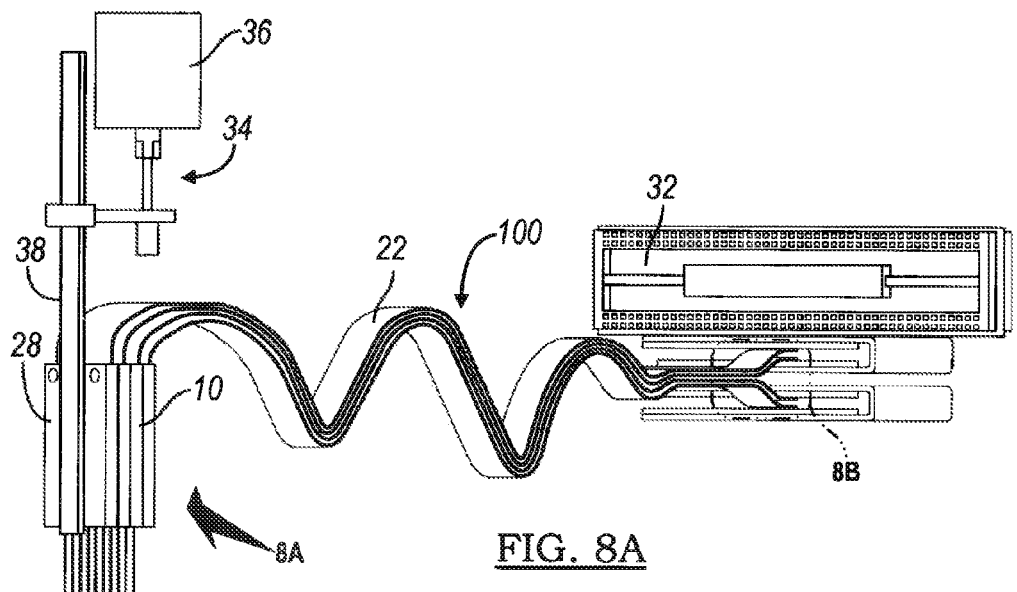
FIGS. 8A to 8C are a representation of the electrode lead system of the preferred embodiment including a series of shims and a series of components, an enlarged view of a representation of a shim, and an enlarged view of a representation of a series of second components, respectively.
Figure 9:
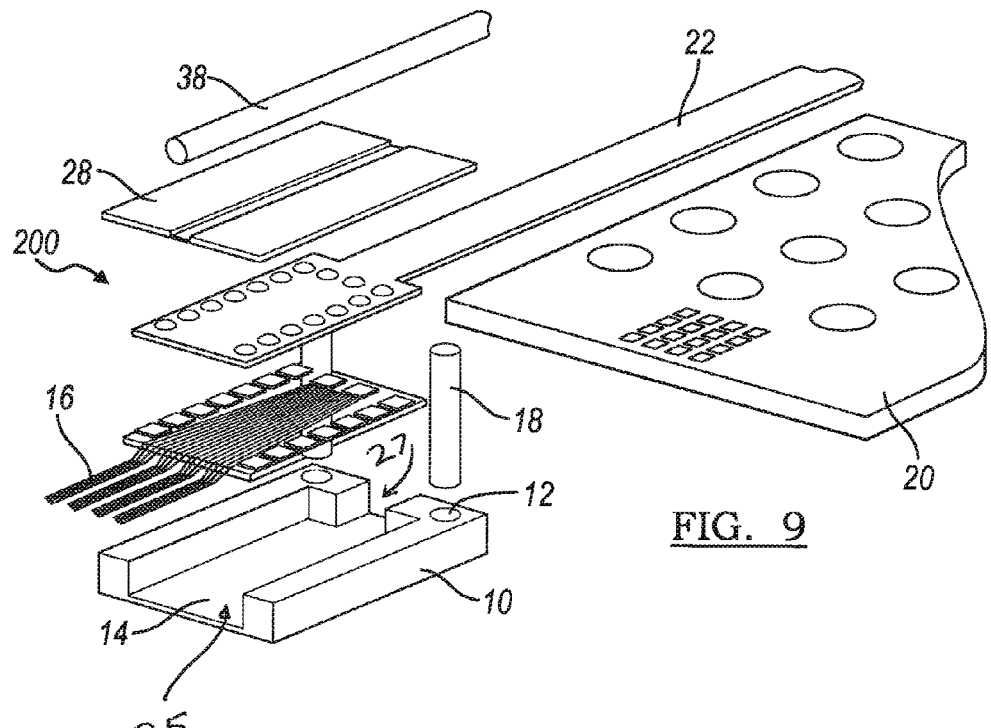
FIG. 9 is an exploded view of a subassembly of the electrode lead system of the preferred embodiment.

Additionally, the electrode lead system 100 may further include an enclosure element, such as a cover 28 as shown in FIGS. 8A and 9, that protects the shims 10 and components 16 individually and/or the entire assembled electrode lead system 100. The cover 28 may also include attachment/alignment feature to allow for temperate or permanent interface to handle the assembled electrode lead assembly.

5. Method of Assembly

Figure 13:
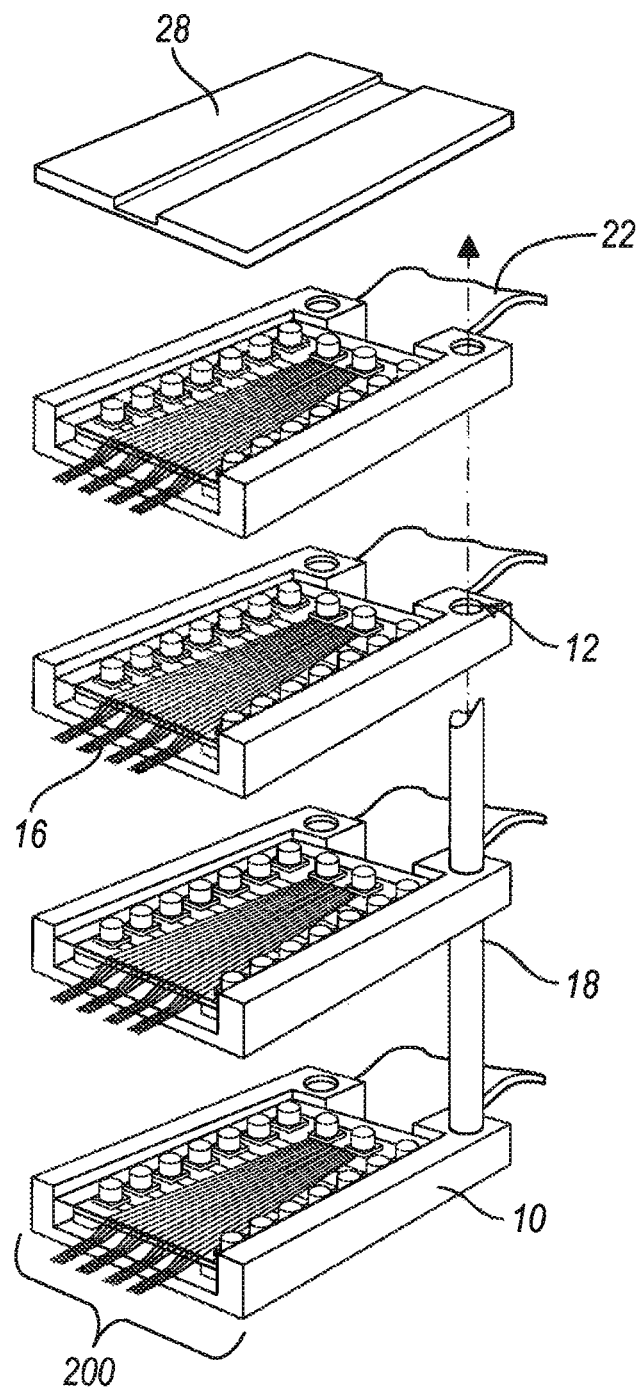
FIG. 13 is an exploded view of a series of subassemblies of the electrode lead system of the preferred embodiment.

The method of assembling the electrode lead systems 100 of the preferred embodiments includes assembling a subassembly 200 (as shown in FIG. 9) and assembling multiple subassemblies 200 (as shown in FIG. 13) to form an electrode lead system 100. The method is preferably designed for the assembly of the electrode lead system 100 of the preferred embodiments. The method, however, may be alternatively used in any suitable environment and for any suitable reason.

As shown in FIG. 9, assembling a subassembly 200 includes the steps of providing a shim 10, coupling a component 16 to a shim 10, coupling a connector 22 to the component 16, and coupling a second component 20 to the connector 22. In that respect, the sidewall 15 thickness is sufficient to receive a first portion of a first electrical component extending beyond the sidewall at a first recess 25 and a second portion of a second electrical component extending beyond the sidewall at a second recess 27.

The steps that include providing a shim 10 and coupling a component 16 to a shim 10, function to couple a component 16 to a shim 10 with a component receptacle 14 adapted to receive that component 16, as shown in FIG. 6. The component 16 is preferably coupled to the shim 10 by gluing them together using any suitable adhesive, such as epoxy. The component 16 may alternatively be coupled to the shim 10 in any suitable fashion or may be fabricated directly onto the shim 10. Some shims 10 in this step may not include a component receptacle 14 and/or may not have a component 16 coupled to them, such that some shims 10 remain empty or blank and function as a spacer.

The steps that include coupling a connector 22 to the component 16 and a second component 20 to the connector 22 couples the second component 20 to the component 16. The connector 22 is preferably connected to the component 16 and the second component 20 via ball bonds or any suitable electrical and/or mechanical connection, or may alternatively be connected in any other suitable fashion. The resulting subassembly 200 is then preferably subjected to an inspection to evaluate its structural and functional characteristics. The alignment of the component 16/connector 22 with respect to the shim 10, as well as the overall structure of the subassembly 200, is preferably inspected using either optical or scanning electron microscopy (SEM). The subassembly 200 may also undergo an electrical test to filter out defective devices before being integrated to the electrode lead assembly 100. The electrical test is preferably impedance spectroscopy. Alternative electrical tests such as cyclic voltammetry may also be performed in conjunction or in place of the impedance spectroscopy. The junction between the component 16 and the connector 22 is preferably countersunk completely within the component receptacle 14 of the shim 10, while the floor of the component receptacle 14 is preferably thick enough to maintain sufficient mechanical stability of the shim.

Figure 7:
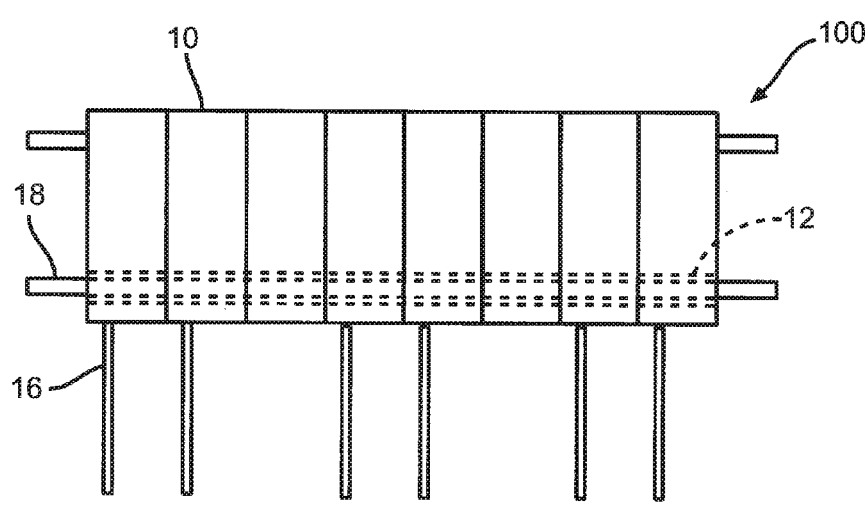
FIG. 7 is a representation of the electrode lead system of the preferred embodiment including a series of shims, a series of components, and a first variation of the alignment element.

As shown in FIG. 13, assembling multiple subassemblies 200 to form an electrode lead assembly 100 includes the steps of coupling a series of shims 10 (each with and/or without components 16) to each other, and coupling the series of second components 20 to a third component 26. As shown in FIG. 7, the step that includes coupling a series of shims 10 functions to assemble a series of components 16 into a three dimensional arrangement. The shims 10 are preferably coupled to one another by gluing them together using any suitable adhesive, such as epoxy. The series of shims 10 may alternatively be coupled in any suitable fashion or may be fabricated directly together. In this step, the alignment features 12 of each shim 10 function to provide an alignment guide such that the multiple shims 10 may be assembled together like building blocks.

The alignment features may further require an additional element such as an alignment element 18. As shown in FIG. 7, the alignment element 18 is a pin that functions to fit through the alignment elements 12 of each shim 10 and thereby aligning the series of shims 10. The alignment element 18 in this variation is preferably made from annealed titanium wire (Small Parts, Miramar, Fla.) TIW-0050 with an outer diameter of 125 μm, but may alternatively be any suitable material with any suitable geometry. The alignment elements 18 are preferably cut to length based on the number of subassemblies 200 to be assembled together. The alignment element may alternatively be any suitable element that functions to provide an alignment guide and or additional alignment feature such that the multiple shims 10 may be assembled together. The alignment element 18 may be kept within the resulting structure, or removed before implantation.

The alignment features may further require an additional element such as a jig, preferably made from TEFLON, which provides additional alignment for the assembly process. The jig preferably anchors the alignment elements 18 at a spacing that matches the alignment features 12 in the shim. With the alignment elements 18 installed, each validated subassembly 200 is preferably positioned and placed over the alignment elements 18 into the jig. A cover 28 is preferably placed over the last subassembly 200 and functions to protect the components 16 and the component 16/connector 22 junctions. Alternatively, the jig could also include a cavity allowing the subassembly 200 to be precisely stacked by utilizing a variation of alignment feature such as the geometric shape of the shims. The jig may also include a clamp mechanism that can be adjusted to tightly but gently hold the components 16 in place and in perfect alignment during the assembly and during the subsequent oven curing process. The tip of the clamp is preferably composed of a low tension spring or a silicone bead in order to hold the electrode lead assembly 100 together at minimal pressure to prevent breakage. Alternatively, a band or string, such as an elastic rubber band, may be used to hold the stacked subassemblies prior to applying the adhesive. With the clamp in place, each subassembly 200 is preferably backfilled with epoxy through the injection ports 24. Surface tension and capillary action will preferably draw epoxy into the shim cavities and component receptacles 14. The entire jig is then preferably placed in an oven to cure the epoxy.

The second components 20 can be electrically and mechanically coupled to the third components 26 preferably by non-permanent connectors such as an anisotropic connector or commercially available connectors. Alternatively, the second components 20 can be permanently coupled to the third component 26 preferably via various soldering techniques, anisotropic-adhesive-film, conductive epoxy, or ultrasonic ball bonding. To reduce the footprint of the assembled third component 26, the connection region can be folded as shown in FIG. 14C if the PCB of the third component 26 is made of a flexible substrate. To reduce stress applied to the connector 22 after folding the connection region, a portion of the second components 20 are preferably flipped and their respective connectors 22 are preferably twisted prior to folding. The assembly 30 is then fixed and insulated with epoxy (such as EpoTek, 353ND-T).

6. The Insertion Tool

Figure 8B:
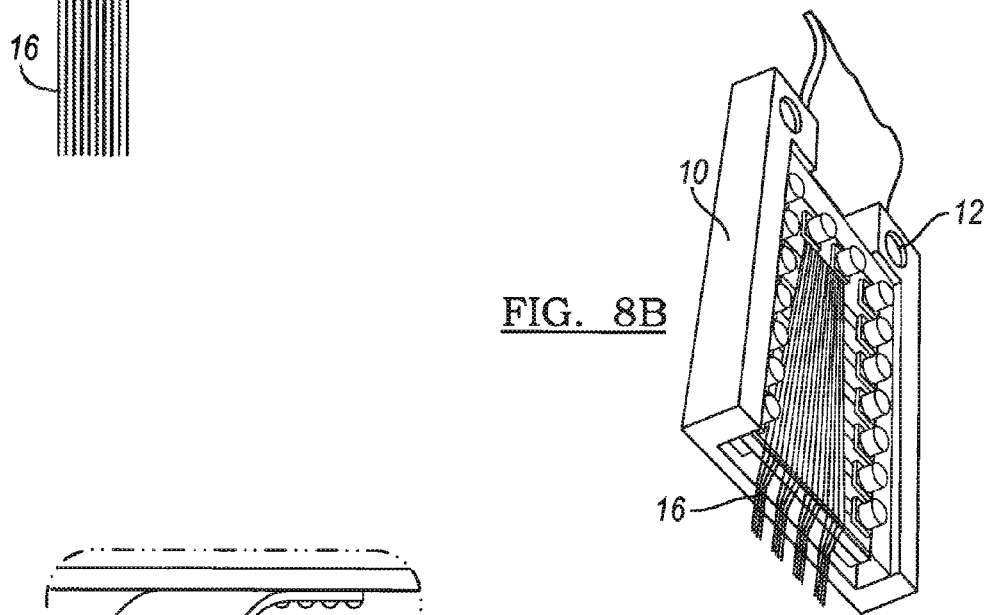
Figure 8C:
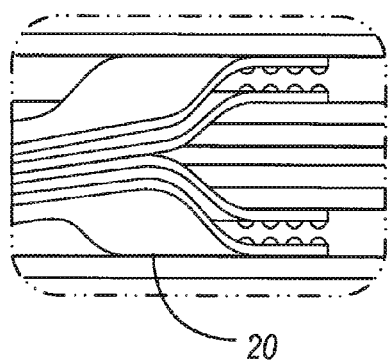

The electrode lead system 100 of the preferred embodiment is preferably designed for an implantable electrode lead system to interface with brain tissue, and more specifically, for an implantable electrode lead system that can interface with brain tissue in a three-dimensional manner. As shown in FIG. 8, the electrode lead system 100 preferably further includes an insertion tool 34 that functions to insert the electrode lead system 100 into brain tissue or any other suitable tissue. The insertion tool 34 preferably includes an insertion driver 36 that functions to move the series of components 16 of the electrode lead system 100 into the tissue at a predetermined speed and an insertion bar 38 that functions to couple the insertion driver 36 to the electrode lead system 100.

The insertion driver 36 can preferably be mounted to a standard stereotactic frame and is preferably one of several variations. In a first variation, the insertion driver is a stepper-motor based actuator, such as a M-230 from Physik Instrumente (Auburn, Mass.). The stepper-motor of this variation is preferably DC powered, offers a travel range of at least 25 mm with step resolution of at least 50 nm, and travel speeds up to about 2 mm/sec. The driver preferably includes a motor controller with computer interface to achieve precise travel distance at programmable speeds. In a second variation, the insertion driver 36 is preferably a high-velocity inserter such as a pneumatic inserter or a spring-loaded inserter.

The insertion bar 38 is preferably coupled to the cover 28, as shown in FIGS. 8 and 9. The I/O assembly 30 may also be temporarily mounted to the insertion bar 38 during the insertion of the electrode lead system 100 into the tissue. A temperature-sensitive polymer (such as polyethylene glycol or PEG) is preferably used to temporarily mount the insertion bar 38 to the electrode lead system 100. After insertion, the insertion bar 38 can preferably be released from the electrode lead system 100 by dissolving away the polymer by applying warm, sterile saline. The insertion bar 38 may alternatively be removed from the electrode lead system 100 in any other suitable fashion, or the insertion bar 38 itself may dissolve or degrade once implanted. Alternatively, the alignment feature 18 can also be used to handle the electrode lead system 100 without the insertion bar 38.

Although omitted for conciseness, the preferred embodiments include every combination and permutation of the various electrode lead systems, the various shims, the various alignment features, the various component receptacles, the various components, the various methods of making and assembly, and the various alignment elements.

As a person skilled in the art will recognize from the previous detailed description and from the figures and claims, modifications and changes can be made to the preferred embodiments of the invention without departing from the scope of this invention defined in the following claims.

What is claimed is:

1. A shim assembly for an implantable electrode lead, the shim assembly comprising:
   a) a first shim surface spaced apart from a second shim surface by a shim sidewall having a sidewall thickness; and
   b) at least a first recess in the shim sidewall spaced apart from a second recess in the shim sidewall, both the first and second sidewall recesses residing at the first shim surface and extending into a portion of the sidewall thickness, but spaced from the second shim surface; and
   c) a receptacle that is open to the first shim surface and meets the first and second recesses at the shim sidewall, wherein the receptacle has a depth that only extends part way through the sidewall thickness so that the receptacle does not meet the second shim surface.

2. The shim assembly of claim 1 wherein at least one of the first and second shim surfaces is planar.

3. The shim assembly of claim 1 wherein the shim is of a material selected from the group consisting of silicon, gallium arsenide, and indium phosphide.

4. The shim assembly of claim 1 wherein the receptacle is a cross-shaped cavity.

5. The shim assembly of claim 1 further comprising a cover that is positionable over the receptacle.

6. The shim assembly of claim 1 wherein the second shim surface opposite the receptacle comprises at least one of a protrusion and a hole.

7. The shim assembly of claim 1 wherein the sidewall thickness is sufficient to receive a first portion of a first electrical component extending beyond the sidewall at the first recess and a second portion of a second electrical component extending beyond the sidewall at the second recess.

8. The shim assembly of claim 1 wherein the first shim surface having the receptacle further comprises at least one of a protrusion and a hole that is not in communication with the first and second shim recesses or with the receptacle.

9. The shim assembly of claim 8 wherein the hole provided in one of the upper and lower shim surfaces is located between the receptacle and the shim sidewall and wherein the hole extends either part way into or completely through the thickness of the shim.

10. The shim assembly of claim 8 wherein the protrusion and hole comprise male and female mating elements.

11. An implantable electrode lead assembly, which comprises:
  a) a shim comprising:
    i) a first shim surface spaced apart from a second shim surface by a shim sidewall having a sidewall thickness; and
    ii) at least a first recess in the shim sidewall spaced apart from a second recess in the shim sidewall, both the first and second recesses residing at the first shim surface and extending into a portion of the sidewall thickness, but spaced from the second shim surface; and
    iii) a receptacle that is open to the first shim surface and meets the first and second recesses at the shim sidewall, wherein the receptacle has a depth that only extends part way through the sidewall thickness so that the receptacle does not meet the second shim surface,
    iv) wherein the first shim surface having the receptacle further comprises one of a protrusion and a hole that is not in communication with the first and second shim recesses or with the receptacle;
  b) at least one first electrical component comprising a first head portion received in the receptacle, wherein a first lead portion extending from the first head portion out beyond the shim sidewall at the first recess; and
  c) at least one second electrical, component comprising a second head portion received in the receptacle, wherein a second lead portion extending from the second head portion extends out beyond the shim sidewall at the second recess.

12. The implantable electrode lead assembly of claim 11 further comprising an insertion bar that is configured to couple to the first electrical component and an insertion driver that is configured to move the insertion bar and thereby the first electrical component into the tissues of a patient.

13. The implantable electrode lead assembly of claim 11 wherein the first electrical component is comprised of neural interface electrode arrays configured to perform at least one of the group consisting of stimulation, recording, chemical sensing, and drug delivery.

14. The implantable electrode lead assembly of claim 13 wherein the neural interface electrode arrays are made of a thin-film polymer substrate.

15. The implantable electrode lead assembly of claim 11 wherein a ratio of the at least one second electrical component to the at least one first electrical component is approximately 1:1.

16. The implantable electrode lead assembly of claim 11 wherein the second electrical component comprises a flexible printed circuit board with integrated circuits.

17. The implantable electrode lead assembly of claim 11 wherein the second electrical component comprises an interconnection that is configured to facilitate mutual coupling between at least two second electrical components.

18. The implantable electrode lead assembly of claim 11 further comprising a third electrical component coupled to the second electrical component, wherein the third electrical component comprises an input/output printed circuit board.

19. The implantable electrode lead assembly of claim 11 wherein a connector electrically connects the first electrical component to the second electrical component.

20. The implantable electrode lead assembly of claim 19 wherein the first electrical component is made of a silicon material, and wherein the connector is a ribbon cable that is integrated with the first and second electrical components.

21. The implantable electrode lead assembly of claim 19 wherein the second electrical component is configured to control the first electrical component via the connector.

22. The implantable electrode lead assembly of claim 11 wherein at least one of the first and second head portions of the respective first and second electrical components is a bond pad.

23. The implantable electrode lead assembly of claim 11 wherein the receptacle depth is sufficient to receive the first and second head portions of the respective first and second electrical components and a third head portion of a third electrical component, wherein a third lead portion extending from the third head portion extends out beyond the shim sidewall at one of the first and second recesses.

24. An implantable electrode lead assembly, which comprises:
  a) at least a first shim and at least a second shim, both shims comprising:
    i) a first shim surface spaced apart from a second shim surface by a shim sidewall having a sidewall thickness; and
    ii) at least a first recess in the shim sidewall spaced apart from a second recess in the shim sidewall, both the first and second sidewall recesses residing at the first shim surface and extending into a portion of the sidewall thickness, but spaced from the second shim surface; and
    iii) a receptacle that is open to the first shim surface and meets the first and second recesses at the shim sidewall, wherein the receptacle has a depth that only extends part way through the sidewall thickness so that the receptacle does not meet the second sidewall surface,
    iv) wherein the first shim surface having the receptacle further comprises one of a protrusion and a hole that is not in communication with the first and second shim recesses or with the receptacle;
  b) a first electrical component comprising a first head portion received in the first receptacle of the first shim with a first lead portion extending from the first head portion out beyond the shim sidewall at the first recess of the first shim and a second electrical component comprising a second head portion received in the first receptacle of the first shim with a second lead portion extending from the second head portion out beyond the shim sidewall at the second recess of the first shim; and
  c) a third electrical component comprising a third head portion received in the second receptacle of the second shim with a third lead portion extending from the third head portion out beyond the shim sidewall at the first recess of the second shim and a fourth electrical component comprising a fourth head portion received in the second receptacle of the second shim with a fourth lead portion extending from the fourth head portion out beyond the shim sidewall at the second recess of the second shim, d) wherein the first and second shims are connected to each other with the protrusion of one of the first and second shims received in the hole of the other shim.

25. The implantable electrode lead assembly of claim 24 wherein the ratio of at least the first and second shims to their respective first and second or third and fourth electrical components is approximately 1:1.

26. The implantable electrode lead assembly of claim 24 wherein a connector electrically connects at least one of the first electrical component to the second electrical component or the third electrical component to the fourth electrical component.

* * * * *